United States Patent [19]

Hoehn et al.

[11] 3,994,898
[45] Nov. 30, 1976

[54] 1,2,4-TRIAZOLO (4,3-b) PYRIDAZIN-3-ONES

[75] Inventors: Hans Hoehn, Tegernheim; Ernst Schülze, Regensburg, both of Germany

[73] Assignee: E. R. Squibb & Sons, Inc., Princeton, N.J.

[22] Filed: Oct. 16, 1975

[21] Appl. No.: 623,124

[52] U.S. Cl. .................. 260/268 BC; 260/250 A; 260/250 AC; 424/250
[51] Int. Cl.² ........................................ C07D 487/04
[58] Field of Search ............... 260/250 AC, 268 BC

[56] References Cited
UNITED STATES PATENTS
3,915,968  10/1975  Bellasio .................... 260/250 AC OTHER PUBLICATIONS
Berger et al, Medicinal Chem., pt. 2, 3rd Ed., pp. 1588–1589 (1971)

Deev et al, Chem. Abst. 77, 164,612s (1972).

*Primary Examiner*—Richard J. Gallagher
*Assistant Examiner*—Mark L. Berch
*Attorney, Agent, or Firm*—Lawrence S. Levinson; Merle J. Smith

[57] ABSTRACT

The new derivatives of 1,2,4-triazolo[4,3-*b*]pyridazin-3-ones and their salts which have the general formula

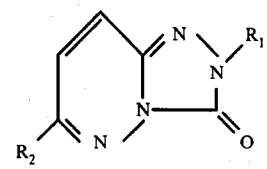

wherein $R_1$ represents hydrogen or lower alkyl, and $R_2$ represents acyclic or cyclic amine groups, are useful as psychotropic, anti-inflammatory and hypotensive agents.

13 Claims, No Drawings

1,2,4-TRIAZOLO (4,3-B) PYRIDAZIN-3-ONES

SUMMARY OF THE INVENTION

The invention relates to new 1,2,4-triazolo[4,3-b]-pyridazin-3-ones and salts thereof having the formula (I)

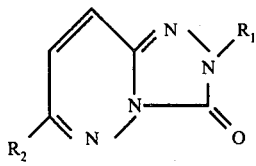

$R_1$ represents hydrogen or lower alkyl;
$R_2$ represents acyclic or cyclic amine groups.

Detailed Description of the Invention

The lower alkyl groups are straight or branched chain hydrocarbon radicals of up to seven carbon atoms, e.g., methyl, ethyl, propyl, isopropyl, butyl, isobutyl, t-butyl, pentyl, hexyl, heptyl, etc. The $C_1$–$C_5$ alkyl groups are preferred, especially the $C_1$–$C_4$ alkyl groups, and most especially methyl and butyl (the latter both straight and branched chain).

The acyclic and cyclic amine groups represented by $R_2$ are those having the formula

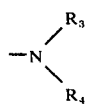

wherein $R_3$ and $R_4$ are independently selected from the group hydrogen, lower alkyl or (hydroxy)lower alkyl or $R_3$ and $R_4$ together with the nitrogen complete one of the heterocyclics pyrrolidine, piperidine or piperazine, unsubstituted or substituted with a lower alkyl or (hydroxy)lower alkyl group.

In the case of $R_3$ and $R_4$, the $C_1$–$C_5$ lower alkyl groups are preferred, especially methyl and butyl (both straight and branched chain). Preferably only one of $R_3$ and $R_4$ is other than hydrogen, especially if the nitrogen substituent is (hydroxy)lower alkyl, although not limited to that. The hydroxy substituent can be either on the terminal or a central carbon of the lower alkyl group, which is also preferably up to five carbons in chain length.

The symbols have the foregoing meanings throughout this specification.

The new compounds of formula I can be produced by several methods.

According to one procedure a product of formula I is obtained by the following reaction steps.

A halo-6-hydrazinopyridazine of the formula (II)

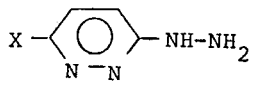

wherein X is halogen, preferably chlorine or bromine and especially chlorine [prepared according to the procedure described in Helv. Chim. Acta, Vol. XXXVII, 132 (1954)], is treated with a haloformic acid ester of the formula (III)

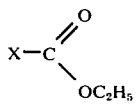

wherein X is a halogen atom as above, to give the halohydrazino pyridazine ester of the formula (IV)

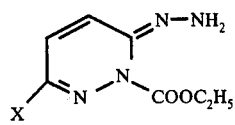

Cyclization of the ester of formula IV in the presence of an alcoholate, e.g., an alkali metal alcoholate like sodium ethylate yields the triazolopyridazinone of the formula (V)

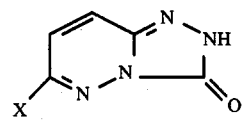

The substituents $R_1$ and $R_2$ can then be introduced, respectively, on the compound of formula V. Treatment of the compound of formula V with an amine

e.g., in an inert organic solvent like dimethylformamide at an elevated temperature, preferably about reflux temperature, results in the replacement of the halogen and yields a product of formula I wherein $R_2$ is an acyclic or cyclic amine radical.

Alkylation of the compound of formula v, or of the $R_2$-substituted product derived therefrom as described above, with an alkylating agent such as a lower alkyl halide like methyl iodide, ethyl iodide or the like, in the presence of a base like potassium carbonate, yields a product with a lower alkyl group in the 2-position ($R_1$ = lower alkyl).

According to an alternate procedure, a product of formula I is produced from a pyridazine compound of the formula (VI)

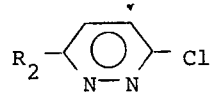

(prepared according to the procedure of Helv. Chim. Acta, supra).

Reaction of the pyridazine of formula VI with a monocarbalkoxy hydrazine of the formula <div align="right">

$NH_2$-NH-COO-lower alkyl       (VII)

</div>

[prepared according to the procedure described in Chem. Ber. 47, 2186 (1914)] results in the formation of an $R_2$-substituted triazolopyridazinone of formula I in which $R_1$ represents hydrogen, e.g.:

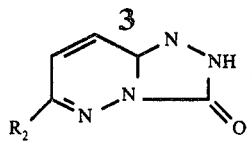

In order to obtain the $R_1$-substituted compound of formula I, the $R_2$-substituted triazolopyridazinone of formula Ia is alkylated by means of an alkyl halide, e.g., alkyl chloride, bromide or iodide, in the presence of a base, e.g., potassium carbonate, as described above.

The new compounds of formula I form salts which are also part of this invention. The salts include acid addition salts, particularly the non-toxic, physiologically acceptable members. These salts are formed by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent of acid.

Certain members, as indicated in the examples, form salts with metals, e.g., alkali metals like sodium, alkaline earth metals like calcium and magnesium, etc. These salts are useful to form soluble derivatives or as intermediates. They are also within the scope of the invention.

Additional experimental details are found in the examples.

The new compounds of this invention are psychotropic agents and can be used as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 2 to 15 mg. per kilogram per day, is appropriate.

The new compounds of this invention also have antiinflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single to 2 to 4 divided doses, as indicated by the carageenan edema assay in rats.

The compounds of formula I also have oral cardiovascular effects and at a dosage in the range of about 10 to 40 mg/kg. can be used as hypotensive and anti- anginal agents, e.g., at 25 mg/kg in the dog moderate hypotension and bradycardia is shown.

The compounds of the invention can be utilized by formulation in tablets, capsules or elixirs for oral administration or in sterile solutions or suspensions for parenteral administration. About 10 to 250 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion or cream containing about 0.1 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

6-Chloro-1,2,4-triazolo[4,3-b]pyridazin-3(2H)-one a. 6-Chloro-3-oxo-1,2,4-triazolo[4,3-b]pyridazine-2(3H)carboxylic acid, ethyl ester and 3-chloro-6-hydrazino1(6H)pyridazinecarboxylic acid, ethyl ester 102.2 g. of 3-chloro-6-hydrazinopyridazine (0.7 mol.) are suspended in a solution of 1400 ml. of absolute ethanol and 77.8 g. of triethylamine (0.77 mol.) with stirring. 83.5 g. of chloroformic acid ethyl ester (0.77 mol.) are added dropwise so that the temperature of the mixture does not exceed 30°. During the addition of the ester the suspended material dissolves. The solution is kept at room temperature for about 2 hours at which time 9.4 g. of a solid precipitates. It consists of 6-chloro-3-oxo-1,2,4-triazolo[4,3-b]pyridazine2(3H)-carboxylic acid, ethyl ester (m. p. 199°–200°/absolute alcohol) and is filtered off. The filtrate is concentrated to dryness, and the residue is treated with about 800 ml. of water, filtered off and dried to give 96 g. (63.4%)

of 3-chloro-6-hydrazino-1(6H)pyridazinecarboxylic acid, ethyl ester, m.p. 156°–158°.

b. 6-Chloro-1,2,4-triazolo[4,3-b]pyridazin-3(2H)-one 39 g. of 3-chloro-6-hydrazino-1(6H)pyridazinecarboxylic acid, ethyl ester (0.18 mol.) are added to a solution of 4.9 g. of sodium (0.216 mol.) in 400 ml. of absolute ethanol and the mixture is then refluxed for 4 hours with stirring. After cooling, the sodium salt of 6-chloro-1,2,4,-triazolo[4,3-b]pyridazin-3(2H)-one is filtered off, washed with ether and, after drying, dissolved in water. Acidification with acetic acid (25%) precipitates the free compound which then is filtered off, washed with water and dried, yielding 26 g. (85%) of 6-chloro-1,2,4-triazolo[4,3-b]pyridazin-3(2H)one, which is recrystallized from ethanol, m.p. 273°–274°.

EXAMPLE 2

6-Chloro-2-ethyl-1,2,4-triazolo[4,3-b]pyridazin-3(2H)one

A mixture of 15.2 g. of the sodium salt of 6-chloro1,2,4-triazolo[4,3-b]pyridazin-3(2H)-one (0.08 mol.) and 16.2 g. of ethyl iodide (0.104 mol.) in 150 ml. of dimethylformamide are heated at 55°–60° for 8 hours with stirring. After cooling, the solvent is removed in vacuo, the residue is treated with water, then filtered off and dried. Recrystallization from benzene yields 9.9 g. (62.5%) of 6-chloro-2-ethyl-1,2,4-triazolo[4,3-b]pyridazin-3(2H)-one, m.p. 150°–152°.

EXAMPLE 3

6-Butylamino-1,2,4-triazolo[4,3-b]pyridazine-3(2H)-one 17 g. of 6-chloro-1,2,4-triazolo[4,3-b]pyridazin-3(2H)-one (0.1 mol.) and 150 ml. of n-butylamine are refluxed for 5 hours. The clear solution is evaporated in vacuo and the oily residue is dissolved in 250 ml. of water. After treating with charcoal, the aqueous solution is acidified with dilute hydrochloric acid to give 18.6 g. (90%) of 6-butylamino-1,2,4-triazolo[4,3-b]pyridazin-3(2H)-one, which, after recrystallization from a mixture of acetonitrile and methanol (1:1), melts at 259°–261°.

EXAMPLE 4

6-Butylamino-2-ethyl-1,2,4-triazolo[4,3-b]pyridazin-3(2H)-one

A mixture of 15 g. of 6-n-butylamino-1,2,4-triazolo-[4,3-b]pyridazin-3(2H)-one (0.075 mol.) and 52 g. of powdered potassium carbonate (0.375 mol.) in 200 ml. of dimethylformamide are heated at 60° for 1 hour with stirring to obtain the potassium salt. Then 30 g. of ethyl iodide (0.187 mol.) are added to the mixture and the whole mixture is kept at 60° for an additional 22 hours. After cooling, the inorganic material is filtered off and the filtrate is evaporated to dryness. The residual 6-n-butylamino-2-ethyl-1,2,4-triazolo[4,3-b]pyridazin-3(2H)-one is treated with water, filtered off, dried and then recrystallized from ethyl acetate to give 12.4 g. (70.5%) of product, m.p. 168°–169°.

EXAMPLE 5

6-Butylamino-2-propyl-1,2,4-triazolo[4,3-b]pyridazin-3(2H)-one

By reacting the product of Example 3 with propyl bromide according to the procedure of Example 4, 6-n-butylamino-2-propyl-1,2,4-triazolo[4,3-b]pyridazin-3(2H)-one is obtained, yield 86%, m.p. 183°–185° (ethyl acetate with some drops of absolute ethanol). The hydrochloride is obtained by treatment with ethanolic HCl.

EXAMPLE 6

6-Methylamino-1,2,4-triazolo[4,3-b]pyridazin-3(2H)-one 20.5 g. of 6-chloro-1,2,4-triazolo[4,3-b]pyridazin-3(2H)-one (0.12 mol.) and a solution of 14.85 g. of methylamine (0.48 mol.) in 160 ml. of benzene are heated in an autoclave at 120° for 5 hours. After cooling, the precipitated product is filtered off and the filtrate is evaporated to dryness. Both portions of 6-methylamino-1,2,4-triazolo[4,3-b]pyridazin-3(2H)-one are treated with dilute aqueous hydrochloric acid, filtered off and recrystallized from water to give 15.8 g. (80%) of material, m.p. > 348°.

EXAMPLE 7

6-[(1-Methylpropyl)amino]-1,2,4-triazolo[4,3-b]pyridazin-3(2H)-one 13.8 g. of 3-chloro-6-(1-methylpropyl)aminopyridazine (0.075 mol.) mixed with 15.6 g. of monocarbethoxy hydrazine (0.15 mol.) are heated to 150°–155° (bath temperature). After about 10 minutes, the fusion takes place, noticeable by a violent reaction and an increase of the temperature of the reaction mixture to 220°–225°. The melted mass is kept for 10 minutes at this temperature and then cooled down to room temperature. The reaction mixture in the flask is dissolved in 75 ml. of water and the solution is set aside for about 20 minutes at which time 6.7 g. (43%) of 6-[(1-methylpropyl)-amino]-1,2,4-triazolo[4,3-b]pyridazin-3(2H)-one precipitate. The product is filtered off, washed with water, dried, treated with acetone, recrystallized from a mixture of acetonitrile and methanol (6:1) and cooled in a refigerator, m.p. 214°–216°.

EXAMPLE 8

6-(4-Methyl-1-piperazinyl)-1,2,4-triazolo[4,3-b]pyridazin-3(2H)-one, hydrochloride (1:1)

A mixture of 17 g. of 3-chloro-6-[1-(4-methylpiperazinyl)]pyridazine (0.08 mol.) and 16 g. of monocarbethoxyhydrazine (0.16 mol.) is heated to 200°–205° (bath temperature) for 20 minutes with stirring. After cooling, the reaction mixture is stirred with 250 ml. of hot ethanol for about 10 minutes and then filtered off. The dried 6-(4-methyl-1-piperazinyl)-1,2,4-triazolo[4,3-b]pyridazin-3(2H)-one, hydrochloride (1:1) is recrystallized from glacial acetic acid; yield 6.2 g. (33%), m.p. 320°–321° (dec.).

EXAMPLE 9

6-[4-(2-hydroxyethyl)-1-piperazinyl]-1,2,4-triazolo[4,3-b]-pyridazine-3(2H)-one

By substituting 3-chloro-6-[1-[4-(2-hydroxyethyl)]-piperazinyl]pyridazine (0.08 mol.) for the 3-chloro-6-[1-(4-methylpiperazinyl)]pyridazine in the procedure of Example 8, 6-[4-(2-hydroxyethyl)-1-piperazinyl]-1,2,4-triazolo[4,3-b]pyridazine-3(2H)-one is obtained.

EXAMPLE 10

6-Pyrrolidino-2-ethyl-1,2,4-triazolo[4,3-b]pyridazine-3(2H)-one

By substituting pyrrolidine for the butylamine in the procedure of Example 3 and then continuing with the procedure of Example 4, 6-pyrrolidino-1,2,4-triazolo[4,3-b]pyridazin-3(2H)-one and 6-pyrrolidino-2-ethyl-1,2,4-triazolo[4,3-b]-pyridazin-3(2H)-one, respectively, are obtained.

EXAMPLE 11

6-(2-Hydroxypropyl)methylamino-1,2,4-triazolo[4,3-b]pyridazin-3(2H)-one

By substituting (2-hydroxypropyl)methylamine for the methylamine in the procedure of Example 6, 6-(2-hydroxypropyl)-methylamino-1,2,4-triazolo[4,3-b]pyridazin-3(2H)-one is obtained.

EXAMPLE 12

6-Piperidino-1,2,4-triazolo[4,3-b]pyridazin-3(2H)-one

By substituting piperidine for the butylamine in the procedure of Example 3, 6-piperidino-1,2,4-triazolo[4,3-b]pyridazin-3(2H)-one is obtained.

EXAMPLE 13

6-Diethylamino-1,2,4-triazolo[4,3-b]pyridazin-3(2H)-one

By substituting diethylamine for the butylamine in the procedure of Example 3, 6-diethylamino-1,2,4-triazolo[4,3-b]pyridazin-3(2H)-one is obtained.

EXAMPLE 14

6-Hexylamino-2-methyl-1,2,4-triazolo[4,3-b]pyridazin-3(2H)-one

By substituting n-hexylamine for the n-butylamine in the procedure of Example 3 and continuing with the procedure of Example 4, but substituting methyl iodide for the ethyl iodide, 6-hexylamino-1,2,4-triazolo[4,3-b]pyridazin-3(2H)-one and 6-hexylamino-2-methyl-1,2,4-triazolo[4,3-b]pyridazin-3(2H)-one, respectively, are obtained.

EXAMPLE 15

6-(2-Hydroxyethyl)amino-2-ethyl-1,2,4-triazolo[4,3-b]pyridazin-3(2H)-one

By substituting ethanolamine for the methylamine in the procedure of Example 6 and then following the procedure of Example 4, 6-[2-hydroxyethyl)amino-1,2,4-triazolo[4,3-b]pyridazin]-3(2H)-one and 6-(2-hydroxyethyl)amino-2-ethyl-1,2,4-triazolo[4,3-b]pyridazin-3(2H)-one are obtained.

EXAMPLE 16

6-(1-Piperazinyl)-1,2,4-triazolo[4,3-b]pyridazin-3(2H)-one, hydrochloride

By substituting 3-chloro-6-(1-piperazinyl)pyridazine (0.08 mol.) for the 3-chloro-6-[1-(4-methylpiperazinyl)]pyridazine in the procedure of Example 8, then continuing as in Example 4, 6-(1-piperazinyl)-1,2,4-triazolo[4,3-b]-pyridazin-3(2H)-one hydrochloride and 6-(1-piperazinyl)-2-ethyl-1,2,4-triazolo[4,3-b]pyridazin-3(2H)-one, respectively, are obtained.

EXAMPLE 17

6-[Di-(2-hydroxyethyl)amino]-1,2,4-triazolo[4,3-b]pyridazin-3(2H)-one

By substituting diethanolamine for the methylamine in the procedure of Example 6, 6-[di(2-hydroxyethyl)amino]-1,2,4-triazolo[4,3-b]pyridazin-3(2H)-one is obtained.

EXAMPLE 18

6-Amino-1,2,4-triazolo[4,3-b]pyridazin-3(2H)-one

By substituting ammonia for the methylamine in the procedure of Example 6, 6-amino-1,2,4-triazolo[4,3-b]-pyridazin-3(2H)-one is obtained.

What is claimed is:

1. A compound of the formula

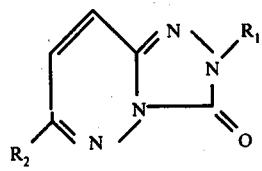

wherein $R_1$ is hydrogen or lower alkyl; and $R_2$ is the group

wherein $R_3$ and $R_4$ each is hydrogen, lower alkyl or (hydroxy)lower alkyl or $R_3$ and $R_4$ together with the nitrogen form one of the heterocyclics pyrrolidine, piperidine or piperazine unsubstituted or substituted with lower alkyl or (hydroxy)lower alkyl; and physiologically acceptable acid addition salts thereof.

2. A compound as in claim 1 wherein $R_1$ is hydrogen.
3. A compound as in claim 1 wherein $R_1$ is lower alkyl.
4. A compound as in claim 1 wherein $R_2$ is lower alkylamino.
5. A compound as in claim 1 wherein $R_2$ is

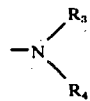

and $R_3$ is lower alkyl and $R_4$ is (hydroxy)lower alkyl.
6. A compound as in claim 4 wherein the lower alkylamino group is butylamino.
7. A compound as in claim 1 wherein $R_1$ is hydrogen and $R_2$ is n-butylamino.
8. A compound as in claim 1 wherein $R_1$ is ethyl and $R_2$ is n-butylamino.
9. A compound as in claim 2 wherein $R_2$ is lower alkylamino.
10. A compound as in claim 9 wherein the lower alkylamino group is methylamino.
11. A compound as in claim 9 wherein the lower alkylamino group is (1-methylpropyl)amino.
12. A compound as in claim 1 wherein $R_1$ is hydrogen and $R_2$ is 4-methylpiperazinyl.
13. A compound as in claim 5 wherein $R_2$ is methyl and $R_4$ is 2-hydroxypropyl and $R_1$ is hydrogen.

* * * * *